United States Patent [19]

O'Sullivan

[11] Patent Number: 4,473,569

[45] Date of Patent: Sep. 25, 1984

[54] PROTECTIVE COMPOSITION FOR USERS OF CYANOACRYLATE ADHESIVES

[76] Inventor: Donncha O'Sullivan, 6 Greenfield Crescent, Donnybrook, Dublin 4, Ireland

[21] Appl. No.: 440,593

[22] Filed: Nov. 10, 1982

[30] Foreign Application Priority Data

Nov. 24, 1981 [IE] Ireland ................... 2753/81

[51] Int. Cl.³ ............... A61K 27/00; A61K 31/185; A61K 31/495
[52] U.S. Cl. ................... 424/248.5; 424/81; 424/250; 424/315
[58] Field of Search ............. 424/81, 248.5, 250, 424/315

[56] References Cited

U.S. PATENT DOCUMENTS

| 3,873,467 | 3/1975 | Hunt | 424/3 X |
|---|---|---|---|
| 4,057,535 | 11/1977 | Lipatova et al. | 424/78 X |
| 4,246,194 | 1/1981 | Furguson | 424/315 X |
| 4,251,387 | 2/1981 | Lim et al. | 424/32 X |

OTHER PUBLICATIONS

Good et al., Biochemistry, 1966, vol. 5, pp. 467–477.

Primary Examiner—Leonard Schenkman
Attorney, Agent, or Firm—Birch, Stewart, Kolasch & Birch

[57] ABSTRACT

A protective composition is provided for application to the skin (especially the hands) of persons working with cyanoacrylate adhesive compositions ("superglues"), to prevent accidental adhesion of skin to skin or to other substrates. The composition comprises a skin-compatible adhesion-inhibiting substance for cyanoacrylate monomers, the substance being incorporated in a conventional topical pharmaceutical base to produce, e.g., a skin cream. Any cyanoacrylate monomer-stabilizer which is kind to the skin can be used, but in addition a group of named zwitterionic aminosulfonic acids ("ZASA's") is proposed and preferred for the purpose. They have a preferred $pK_a$ at in the range of 6.0–8.3 at 20° C.

17 Claims, No Drawings

PROTECTIVE COMPOSITION FOR USERS OF CYANOACRYLATE ADHESIVES

BACKGROUND AND FIELD OF THE INVENTION

This invention relates to precaution against a hazard in the use of adhesive compositions based on cyanoacrylate monomers. It relates in particular to a protective composition for the skin (especially the hands) of a person working with a cyanoacrylate adhesive or "superglue", and to a method using the composition, for protecting such a person's skin.

Cyanoacrylate monomers, as is well known, polymerise rapidly on contact with certain activating substances in trace quantities. These substances include inorganic salts, carbonyl compounds such as urea, and Lewis bases such as water Human perspiration comprises mainly moisture, a small proportion of urea, inorganic salts, and some lactic acid. Human skin normally has a slightly acid reaction, with a pH of 5 to 6. Normal human skin serves as a very effective activating substrate for cyanoacrylate adhesives. There thus arises the notorious hazard involved in the use of these compositions, that traces of the composition on the skin are immediately activated, and skin so contaminated will on contact stick fast to other skin portions or substrate surfaces, with initial cure taking place within a few seconds. Persons thus affected may have great difficulty in freeing themselves, and in severe cases may even require surgical assistance. The problem is well known in factories where parts are assembled by means of "superglues" and the like, but the hazard is perhaps greater when inexperienced persons are handling cyanoacrylates.

It is an object of this invention to provide an easily used protective means to render cyanoacrylate adhesives innocuous to persons using them.

Accordingly, the invention provides a protective composition for the skin of a person working with a cyanoacrylate-type adhesive, which composition comprises a skin-compatible adhesion-inhibiting substance for cyanoacrylate monomers, said substance being incorporated in a dermatologically compatible base for topical application.

DETAILED DESCRIPTION OF THE INVENTION

The adhesion-inhibiting substance may be a skin-compatible conventional stabiliser for cyanoacrylate monomers, but in a preferred embodiment of the invention, said substance comprises at least one zwitterionic aminosulfonic acid (hereinafter ZASA) having a $pK_a$ at 20° C. in the range of 6.0–8.3 (i.e. the molecules of the substance exist mainly in their dipolar form in the pH range 6.0–8.3). These ZASA's permit polymerisation of the adhesive but, surprisingly, they render the resulting solid non-adherent to the skin, so that it can be easily peeled, rubbed or washed off.

The ZASA's so far investigated and found to have the properties necessary for use in compositions of the invention are set out, with their $pK_a$ values and trivial names, in the following list (all $pK_a$ values quoted in this specification are at 20° C.):

| | | |
|---|---|---|
| 2-(N—Morpholinyl)-ethane sulfonic acid | 6.15 | MES |
| N,N—bis-(2-Hydroxyethyl)-2-aminoethane sulfonic acid | 7.15 | BES |
| 2-[N—(N'—2-Hydroxyethyl)-piperazinyl]-ethane sulfonic acid | 7.55 | HEPES |
| 3-[N—(N'—2-Hydroxyethyl)-piperazinyl]-propane sulfonic acid | 8.0 | HEPPS (or EPPS) |
| Piperazine-1,4-bis-(2-ethane sulfonic acid) | 6.8 | PIPES |
| 2-[N—tris-(Hydroxymethyl)-methylamino]-ethane sulfonic acid | 7.5 | TES |

All of them but HEPPS were described among others, by Good N. et al. in Biochemistry 1966, Vol 5, 467. "It is not difficult to synthesise aliphatic amines with appropriate acid dissociation constants"—to quote from the above-cited report. It may be added that the preparation of their aromatic analogues presents no particular difficulty either. To quote further from the report: "It is easy to design and prepare a wide variety of inexpensive compounds" (i.e., hydrogen ion buffers for biological research) "with desired dissociation constants, solubilities and reactivities... Many more could be prepared". All such easily accessible ZASA's, having $pK_a$ values within the above specified limits, are accordingly to be understood as suitable for use in compositions of the present invention, unless disqualified by dermatological incapatibility which, however, is thought to be unlikely.

The proportion of the active ingredient by weight of the composition is in the range 0.05% to 30%, preferably 0.05% to 5.0%, most preferably 0.1% to 1.0%. The topical base is selected from a wide variety of compositions formulated according to known principles for protective, cosmetic and pharmaceutical purposes. Such compositions include creams, solids, lotions and film-forming solutions among others. They may be presented in boxes, jars or squeezable tubes, both collapsible and non-collapsible. The solids may be presented as sticks for rubbing on to the skin. Some of the topical bases may be presented as papers, woven or non-woven fabric pieces, or pads, all impregnated with the composition.

The invention will be appreciated in greater detail from the following examples of specific embodiments thereof.

EXAMPLE 1

A skin cream is made up from the following recipe:

| | | Parts by Weight |
|---|---|---|
| A. | Oil Phase | |
| | Stearic acid | 13.0 |
| | Microcrystalline wax | 6.5 |
| | Olive oil | 3.5 |
| | Glyceryl monostearate (acid-stable grade) | 3.5 |
| | Polyoxyethylene sorbitan monolaurate[1] | 12.0 |
| | Silicone fluid (200–350 centistokes) | 3.0 |
| B. | Aqueous Phase | |
| | HEPES | 0.2 |
| | Water (q.s. ad 100.0) | 58.3 |

[1]The product sold under the trade name TWEEN 20

This cream is rubbed into the hands before working with a cyanoacrylate adhesive composition. It will normally give protection against sticking of the fingers together or to an object being glued, for a working session of 4–5 hours. It is non-greasy and comfortable to use.

EXAMPLE 2

An application stick is made from the following ingredients:

| | Parts by Weight |
|---|---|
| Eutanol G[1] (2-octadodecanol) | 39.0 |
| Comperlan HS[1] (stearic acid monoethanolamide) | 11.0 |
| Stearic acid | 10.0 |
| HEPPS | 5.0 |
| Ethanol 96% v/v | 20.0 |
| Glycerol | 15.0 |

[1]Henkel International, Federal Republic of Germany.

The ingredients other than ethanol are mixed and melted together. The temperature of the melt is brought below 70°, whereupon the ethanol is added and well mixed in. The melt is poured into suitable moulds and allowed to set. The resulting moulded sticks are removed from the moulds, wrapped individually in aluminium foil and packed.

A stick is rubbed on the hands before working with a cyanoacrylate adhesive composition. The protection period is similar to that given by the compositions of the previous Example.

EXAMPLE 3

This example illustrates a typical formulation which can be used for preparing a protective composition in accordance with the invention, using any zwitterionic substances ("ZASA's") which have suitable properties, including those mentioned in the present specification.

| Ingredient | Parts by Weight |
|---|---|
| Stearic acid | 10.05 |
| Vegetable oil (e.g. Sunflower) | 8.0 |
| Glyceryl monostearate (self-emulsifying) | 2.50 |
| Silicone oil (DC Silicone 200/350, Dow Corning) | 0.50 |
| TWEEN 20 (Polyoxyethylene sorbitan monolaurate) | 10.40 |
| The selected "ZASA" | 0.10 to 1.00* |
| Water (q.s. ad 100) | 68.45 to 67.55 |

*A preferred proportion here is 0.55.

The ingredients are put together by known pharmaceutical procedures, such as those set out in the previous examples.

In addition to preservatives, other conventional pharmaceutically acceptable additives may be incorporated in the compositions of the invention. These include, for example, humectants, film formers and water repellents. Sorbitol is a useful humectant. A 4% mucilage of Methyl cellulose is a useful film former. The dimethyl silicones sold by Imperial Chemical Industries Ltd. of the UK under the trade designations F 110 and F 111 are useful water repellents.

Compositions of the invention, when applied to a person's skin, prevent skin-to-skin adhesion, and adhesion of skin to other substrates, when a cyanoacrylate adhesive composition is present as a skin contaminant, or is present on a said substrate. They do not prevent polymerisation of the cyanoacrylate, however. They can be removed from the hands together with the polymerised cyanoacrylate contaminant by a simple soap and water wash.

In the particular case of a composition of the invention which is a skin cream containing both HEPES and HEPPS, it has been found that the proportion of these active ingredients is desirably about 1 part of HEPES to 10 parts of HEPPS by weight. This yields a cream with desirable physical properties.

When one is working with a cyanoacrylate adhesive and using a composition of the invention, one should take care to avoid contamination of the substrate with the composition, before the adhesive is applied thereto. Intended adhesive bonds can be accidentally rendered weak or ineffective by traces of the compositions of the invention.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An adhesion-inhibiting protective composition for the skin of a person working with cyanoacrylate-type adhesives, which composition comprises an adhesion-inhibiting protective amount of at least one Zwitterionic aminosulfonic acid compound, said compound having a $pK_a$ value at 20° C. in the range of 6.0–8.3 and said protective composition being in the form of a cream, solid or lotion.

2. A protective composition as in claim 1, wherein the compound is a member selected from the group consisting of 2-(N-Morpholinyl)-ethane sulfonic acid,
N,N-bis-(2-Hydroxyethyl)-2-aminoethane sulfonic acid,
2[N-(N'-2-Hydroxyethyl)-piperazinyl] ethane sulfonic acid,
3-[N-(N'-2-Hydroxyethyl)-piperazinyl] propane sulfonic acid,
Piperazine-1,4-bis-(2-ethane sulfonic acid), and
2-[N-tris-(Hydroxymethyl)-methylamino]-ethane sulfonic acid.

3. A protective composition as in claim 1, wherein said compound is present in an amount of from 0.05% to about 30% by weight of the composition.

4. A protective composition as in claim 3, wherein said compound is present in an amount of from 0.05% to 5% by weight of the composition.

5. A protective composition as in claim 3, wherein said compound is present in an amount of from 0.1% to 1.0% by weight of the composition.

6. A protective composition as recited in claim 1, wherein said compound is

2-[N-(N'-2-Hydroxyethyl)-piperazinyl]-ethane sulfonic acid.

7. A protective composition as in claim 2, wherein the selected Zwitterionic aminosulfonic acid compounds in said composition are 2-[N-(N'-2-Hydroxyethyl)-piperazinyl]-ethane sulfonic acid and 3-[N-(N'-2-Hydroxyethyl)-piperazinyl]-propane sulfonic acid, in a weight ratio of about 1 to 10, respectively.

8. A protective composition as in claim 1, which is in the form of a hand cream.

9. A protective composition as in claim 2, which is in the form of a hand cream.

10. A protective composition as in claim 1, wherein said composition is in the form of a lotion or stick for application to the skin.

11. A protective composition as in claim 2, wherein said composition is in the form of a lotion or stick for application to the skin.

12. An applicator material selected from the group consisting of papers, woven fabric pieces, non-woven fabric pieces and pads, impregnated with an adhesion-inhibiting protective composition for the skin of a person working with cyanoacrylate-type adhesives, which composition comprises, incorporated in a dermatologically compatible base for topical application, an adhesion-inhibiting protective amount of at least one Zwitterionic aminosulfonic acid compound, said compound having a $pK_a$ value at 20° C. in the range of 6.0–8.3.

13. An applicator material as in claim 12, wherein said Zwitterionic aminosulfonic acid compound is a member selected from the group consisting of 2-(N-Morpholinyl)-ethane sulfonic acid, N,N-bis-(2-Hydroxyethyl)-2-aminoethane sulfonic acid, 2-[N-(N'-2-Hydroxyethyl)-piperazinyl] ethane sulfonic acid, 3-[N-(N'-2-Hydroxyethyl)-piperazinyl] propane sulfonic acid, Piperazine-1,4-bis-(2-ethane sulfonic acid), and 2-[N-tris-(Hydroxymethyl)-methylamino]-ethane sulfonic acid.

14. A method of protecting the skin of a person, working with a cyanoacrylate adhesive, against tissue adhesion, which method comprises applying to said person's skin, before skin contamination with said adhesive has occurred, or can occur, an effective adhesion-inhibiting protective amount of a coating of an adhesion-inhibiting protective composition for the skin of a person working with cyanoacrylate-type adhesives, which composition comprises, incorporated in a dermatologically compatible base for topical application, an adhesion-inhibiting protective amount of at least one Zwitterionic aminosulfonic acid compound, said compound having a $pK_a$ value at 20° C. in the range of 6.0–8.3.

15. A method as in claim 14, wherein said compound is a member selected from the group consisting of 2-(N-Morpholinyl)-ethane sulfonic acid, N,N-bis-(2-Hydroxyethyl)-2-aminoethane sulfonic acid, 2-[N-(N'-2-Hydroxyethyl)-piperazinyl] ethane sulfonic acid, 3-[N-(N'-2-Hydroxyethyl)-piperazinyl] propane sulfonic acid, Piperazine-1,4-bis-(2-ethane sulfonic acid), and 2-[N-tris-(Hydroxymethyl)-methylamino]-ethane sulfonic acid.

16. A method as in claim 14, wherein said compound is 2-[N-(N'-2-Hydroxyethyl)-piperazinyl]-ethane sulfonic acid.

17. A method as in claim 15, wherein the selected compounds are 2-[N-(N'-2-Hydroxyethyl)-piperazinyl]-ethane sulfonic acid and 3-[N-(N'-2-Hydroxyethyl)-piperazinyl]-propane sulfonic acid, in a weight ratio of about 1 to 10, respectively.

* * * * *